(12) United States Patent
Foley et al.

(10) Patent No.: US 10,984,894 B2
(45) Date of Patent: Apr. 20, 2021

(54) AUTOMATED IMAGE QUALITY CONTROL APPARATUS AND METHODS

(71) Applicant: GE Healthcare Limited, Buckinghamshire (GB)

(72) Inventors: Christopher Foley, Amersham (GB); Pal Tezges, Budapest (HU); Laszlo Rusko, Szeged (HU)

(73) Assignee: GE HEALTHCARE LIMITED, Buckinghamshire (GB)

( * ) Notice: Subject to any disclaimer, the term of this patent is extended or adjusted under 35 U.S.C. 154(b) by 197 days.

(21) Appl. No.: 16/233,624

(22) Filed: Dec. 27, 2018

(65) Prior Publication Data

US 2020/0211678 A1    Jul. 2, 2020

(51) Int. Cl.
*G06K 9/00* (2006.01)
*G16H 10/20* (2018.01)
(Continued)

(52) U.S. Cl.
CPC .......... *G16H 10/20* (2018.01); *G06T 7/0014* (2013.01); *G16H 10/60* (2018.01); *G16H 30/20* (2018.01);
(Continued)

(58) Field of Classification Search
CPC ........ G16H 10/60; G06Q 50/24; G06Q 50/22; G06Q 10/10; G06F 19/3418
(Continued)

(56) References Cited

U.S. PATENT DOCUMENTS

| | | |
|---|---|---|
| 2005/0251011 A1 | 11/2005 | Zahlmann et al. |
| 2008/0052112 A1 | 2/2008 | Zahlmann et al. |

(Continued)

FOREIGN PATENT DOCUMENTS

WO    2010001403    1/2010

OTHER PUBLICATIONS

International Searching Authority, "International Search Report and Written Opinion," issued in connection with PCT patent application No. PCT/EP2019/086710, dated Mar. 20, 2020, 15 pages.
(Continued)

*Primary Examiner* — Charlotte M Baker
(74) *Attorney, Agent, or Firm* — Hanley, Flight and Zimmerman, LLC

(57) ABSTRACT

An image quality control system is disclosed. The example system includes an artificial intelligence modeler to process image data and metadata from patient data to generate first feature(s) from the image data and to parse the metadata to identify study information. The example system includes a computer vision processor to identify second feature(s) in the image data. The example system includes a results evaluator to compare the first feature(s) and second feature(s) to generate a comparison and to evaluate the comparison, first feature(s), and second feature(s) with respect to the study information to generate an evaluation. The example system includes a quality controller to compare the evaluation to quality criterion(-ia) to produce an approval or rejection of the patient data, the approval to trigger release of the patient data and the rejection to deny release of the patient data.

20 Claims, 15 Drawing Sheets

(51) Int. Cl.
*G16H 10/60* (2018.01)
*G16H 30/20* (2018.01)
*G16H 30/40* (2018.01)
*G06T 7/00* (2017.01)

(52) U.S. Cl.
CPC ... *G16H 30/40* (2018.01); *G06T 2207/20084* (2013.01)

(58) Field of Classification Search
USPC .......................................................... 382/128
See application file for complete search history.

(56) References Cited

U.S. PATENT DOCUMENTS

| | | |
|---|---|---|
| 2008/0270420 A1 | 10/2008 | Rosenberg |
| 2009/0016579 A1 | 1/2009 | White et al. |
| 2009/0112619 A1 | 4/2009 | Owens et al. |
| 2016/0092748 A1 | 3/2016 | Koktava et al. |
| 2016/0350919 A1 | 12/2016 | Steigauf et al. |
| 2018/0082024 A1* | 3/2018 | Curbera ................. G06F 21/00 |
| 2018/0144214 A1 | 5/2018 | Hsieh et al. |
| 2020/0066391 A1* | 2/2020 | Sachdeva ............... G16H 20/40 |
| 2020/0126215 A1* | 4/2020 | Bronkalla ............ A61B 5/0013 |
| 2020/0137357 A1* | 4/2020 | Kapoustin .......... G06K 9/00255 |
| 2020/0234825 A1* | 7/2020 | Dobson .................. G16H 10/60 |

OTHER PUBLICATIONS

Cagnon et al., "Description and Implementation of a Quality Control Program in an Imaging-Based Clinical Trial," 2006, 11 pages.

Gedamu, "Guidelines for Developing Automated Quality Control Procedures for Brain Magnetic Resonance Images Acquired in Multi-Centre Clinical Trials," Department of Biomedical Engineering and Montreal Neurological Institute, McGill University, 2011, 26 pages.

Gedamu et al., "Automated Quality Control of Brain MR Images," Journal of Magnetic Resonance Imaging, 2008, 12 pages.

Erickson et al., "Imaging in Clinical Trials," Department of Radiology, Mayo Clinic, Spacial Issue—Imaging Informatics, 2007, 6 pages.

\* cited by examiner

AUTOMATED IMAGE QUALITY CONTROL APPARATUS AND METHODS

FIELD OF THE DISCLOSURE

This disclosure relates generally to improved image quality and, more particularly, to improved machine learning apparatus, systems, and methods for medical image processing for quality control.

BACKGROUND

A variety of economy, technological, and administrative hurdles challenge healthcare facilities, such as hospitals, clinics, doctors' offices, etc., to provide quality care to patients. Economic drivers, less skilled staff, fewer staff, complicated equipment, and emerging accreditation for controlling and standardizing radiation exposure dose usage across a healthcare enterprise create difficulties for effective management and use of imaging and information systems for examination, diagnosis, and treatment of patients.

Healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance.

Healthcare provider tasks including image processing and analysis, etc., are time consuming and resource intensive tasks that are impractical, if not impossible, for humans to accomplish alone.

In clinical trials, data quality assurance is a cornerstone of good clinical practice (e.g., as defined by the ICH Good Clinical Practice (GCP) international quality standard, European Medicines Agency (EMA) guidance on GCP quality and quality assurance, etc.). For example, a clinical trial sponsor is responsible for implementing and maintaining quality assurance and quality control systems with written standard operating procedures (SOPs) to help ensure that trials are conducted and data are generated, documented (e.g., recorded), and reported in compliance with the protocol, GCP, and the applicable regulatory requirement(s). With good meta-data, the quality control process can be partly automated. However, this does not verify the actual integrity of the medical image because other critical aspects cannot be validated including checking that the whole anatomic field was included, presence of motion, etc. Further, even if an imaging device is operated correctly, obtained images may still be unacceptable, and, thus, the GCP requirements cannot currently be satisfied without some level of human monitoring.

A visual review of collected images is designed to detect inadequacies in the images that could not be characterized by using technical parameters. It is very important that medical images are validated for acceptability of the image and adherence to technical parameters. These images need to be checked by qualified employees, and this manual review adds extra costs to the quality control process. However, technical quality control can be very time consuming, and mistakes can be made.

BRIEF DESCRIPTION

Certain examples provide systems and methods for image processing and quality control.

Certain examples provide an automated image quality control system. The example system includes an artificial intelligence modeler to process image data and metadata from patient data to generate one or more first features from the image data and to parse the metadata to identify study information. The example system includes a computer vision processor to identify one or more second features in the image data. The example system includes a results evaluator to compare the one or more first features and the one or more second features to generate a comparison and to evaluate the comparison, the one or more first features, and the one or more second features with respect to the study information to generate an evaluation. The example system includes a quality controller to compare the evaluation to one or more quality criterion to produce an approval or rejection of the patient data. The example system includes an output generator to output a representation of the approval or the rejection of the patient data, wherein the approval is to trigger release of the patient data and the rejection is to deny release of the patient data.

Certain examples provide at least one computer-readable storage medium including instructions which, when executed, cause at least one processor to at least: generate, using a first artificial intelligence model, one or more first features from image data included in patient data; parse, using a second artificial intelligence model, metadata included in the patient data to identify study information; identify, using computer vision, one or more second features in the image data; compare the one or more first features and the one or more second features to generate a comparison; evaluate the comparison, the one or more first features, and the one or more second features with respect to the study information to generate an evaluation; compare the evaluation to one or more quality criterion to produce an approval or rejection of the patient data; and output a representation of the approval or the rejection of the patient data, wherein the approval is to trigger release of the patient data and the rejection is to deny release of the patient data.

Certain examples provide a computer-implemented method of image quality control. The example method includes generating, using a first artificial intelligence model, one or more first features from image data included in patient data. The example method includes parsing, using a second artificial intelligence model, metadata included in the patient data to identify study information. The example method includes identifying, using computer vision, one or more second features in the image data. The example method includes comparing, using at least one processor, the one or more first features and the one or more second features to generate a comparison. The example method includes evaluating, using the at least one processor, the comparison, the one or more first features, and the one or more second features with respect to the study information to generate an evaluation. The example method includes comparing, using the at least one processor, the evaluation to one or more quality criterion to produce an approval or rejection of the patient data. The example method includes outputting, using the at least one processor, a representation of the approval or the rejection of the patient data, wherein the approval is to trigger release of the patient data and the rejection is to deny release of the patient data.

BRIEF DESCRIPTION OF THE DRAWINGS

The figures are not scale. Wherever possible, the same reference numbers will be used throughout the drawings and accompanying written description to refer to the same or like parts.

DETAILED DESCRIPTION

Figure 1:
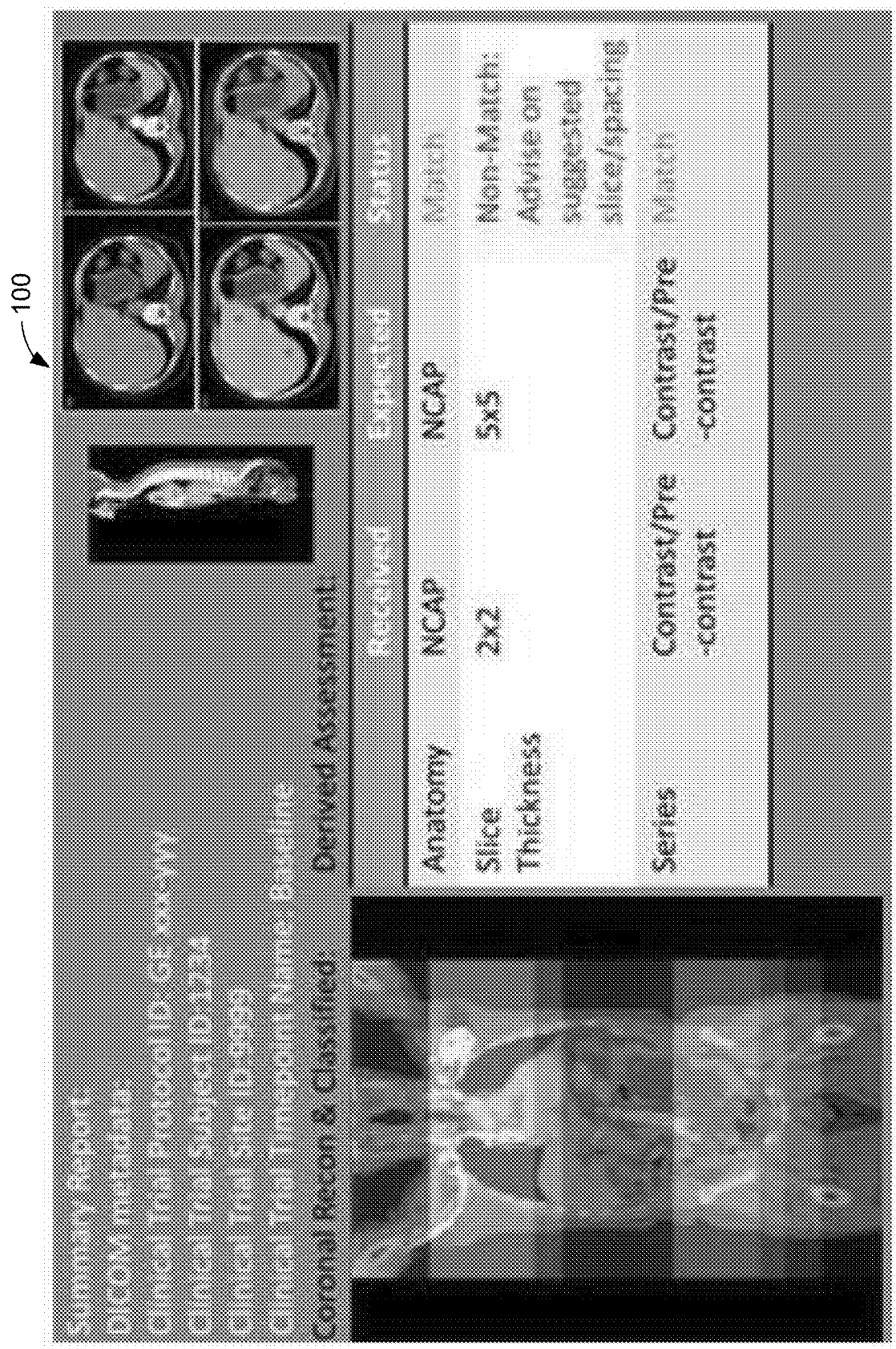
FIG. 1 illustrates an example quality control report.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. OVERVIEW

Imaging devices (e.g., gamma camera, positron emission tomography (PET) scanner, computed tomography (CT) scanner, X-Ray machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning can be used to help configure, monitor, and update the medical imaging workflow and devices.

For example, image quality control is important for diagnostic accuracy, clinical trial robustness, etc. If the hours spent checking the images can be reduced, then the time savings is valuable, especially when processing many medical images. Certain examples automatically process image and related metadata to identify and highlight errors before the associated image(s) are quality controlled. For example, if there is a case that should contain a heart but contains a kidney image instead, certain examples provide systems and methods to detect that a kidney has been imaged instead and will prompt for review and/or corrective action.

Performing image quality checks (QC) in clinical trials or clinical routine is necessary for quality assurance, but QC is an expensive activity because it is a time consuming and manual process driven by a human operator. Certain examples automate image QC checks for significant improvement in quality, accuracy, effectiveness, and timing. For example, image data are typically stored in a DICOM (Digital Imaging and Communications in Medicine) file format, with an exam including multiple DICOM slice instances. DICOM files each include a metadata portion and an image data portion. Quality control checks are concerned with the accuracy and completeness of both the metadata and image data. Certain examples evaluate the quality of both the metadata, which includes information about the study, series equipment, acquisition parameters, and patient information, as well as check the image data using computer vision and deep learning algorithms that detect important image features. Certain examples then compare the metadata, image analysis results, and study criteria and summarize inconsistencies.

DICOM stores various technical information about an image acquisition and image content that can be automatically assessed for quality control. While prior checks required a human visual inspection of acquired images to identify motion or artefacts, acquired anatomy region, contrast usage, presence of required organ, etc., certain examples evaluate image data using associated metadata along with computer vision techniques to form an overall quality assessment against one or more pre-defined criterion (such as a clinical trial study imaging criterion, etc.).

For example, metadata is analyzed from one or more image files (e.g., DICOM files, etc.) to check for data regarding an associated patient, an included image, and how the image and/or other data was acquired, etc. The metadata can include important information that can be configured according to one or more criterion, such as patient details, scanner details, scanning parameters, and contextual/clinical information (contrast, anatomy scanned, etc.). For example, the automated QC process can rely on image metadata generated by the imaging device (e.g., image properties, acquisition parameters, etc.) and validated patient-metadata imported from a system such as a radiology information system (RIS), health information system (HIS), picture archiving and communication system (PACS), laboratory information system (LIS), electronic medical record system (EMR), etc.

Additionally, image information is gathered using deep learning. Deep learning model(s) check for features related to image quality (e.g., low level checks, etc.), patient anatomy and features (e.g., medium level checks), and checks about the patient such as obesity (e.g., high level checks), etc. Image information involves low-level features such as presence of noise, contrast enhancement, artifact, etc.; medium-level features such as presence of anatomy region, organ, landmark, etc.; and high-level features such as presence of obesity, extreme pathology, and implant detection, etc.

The image information facilitates quantitative analytics tailored to an anatomical structure of interest. For example, a structure of interest can be detected/segmented to extract features such as density, contrast, noise, texture, histogram, etc. The structure is classified based on the features (e.g., the low-level features, medium-level features, high-level features, etc.). The image information is compared with metadata to preserve the integrity of a large dataset. For example, the image information is compared with the metadata to detect duplication (e.g., records with a different identifier but same image or patient, etc.), validate metadata information (e.g., contrast-agent indicated for an exam but no contrast found in the associated image, etc.), etc.

Image information can be simplified to facilitate human readability of a large number of images (visual assessment, search, etc.). Simplification of image information includes generating standard two-dimensional (2D) views from three-dimensional (3D) images (e.g., slice or ray-sum), generating a checksum, etc. Identifying information for the associated patient can also be removed. Removal of an individual's identification is important in clinical trials and for other healthcare privacy reasons. Removal of identifying information and/or other deidentification involves detection and modification of metadata (e.g., erase from DICOM header, etc.) as well as image information (e.g., localize and erase a face from an image, etc.). An example resulting QC report 100 is shown in FIG. 1.

Certain examples quickly uncover and highlight issues, providing actors involved with quality control with validation of problems and solutions. Metadata analysis and image analysis both provide technical advantages as they allow for exams to be semi-automatically failed if they do not match expected content, results, etc. The image analysis is specifically useful as it has advantages that checking metadata does not. For example, checking the image information directly can determine whether any partial organs are shown in the image, if the image contains artifacts, etc. In addition to checking the quality of the image, this information can be compared to the metadata to check for inconsistencies, enabling automatic quality control of metadata to reduce processing errors in QC. In certain examples, this QC analysis can be integrated into medical systems to generate notifications, corrections, etc., regarding the QC findings in a clinical setting, a clinical trial setting, etc.

Using deep learning models, images can be classified and organs, anatomic regions, etc., can be localized in image data. Such models can serve as a basis for an automated image QC framework. Results can be adapted to other modalities, organs, etc., and can be extended to other image classification problems.

Thus, certain examples provide an automated image quality checker to evaluate quality (e.g., using accuracy and completion) of metadata and image data. Metadata can include study information, series equipment, acquisition parameters, patient information, etc. The image data is evaluated using computer vision and/or deep learning, for example. Analyzing the image data is done by detecting important image features including low-level features, medium-level features, and high-level features. Once the metadata and the image data has been collected and evaluated, the system/method summarizes any inconsistencies between the different types of data. A comparison against one or more pre-defined criterion is also implemented. For example, image data and metadata can be compared to detect duplication in the image data, validate the metadata, simplify the image information, and generate 2D views from 3D image information. This allows for quicker and more confident patient imaging.

In certain examples, a combination of computer vision and deep learning can be used to determine image quality by leveraging both image data and associated metadata. Rather than image labels and central tendency metrics, certain examples provide a deep learning model to take an image that has been checked and incorporate image metadata and study criteria to summarize inconsistencies with respect to the image.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Certain examples use neural networks and/or other machine learning to implement a new workflow for image analysis including body detection in an image (e.g., a two-dimensional and/or three-dimensional computed tomography (CT), x-ray, etc., image), generation of a bounding box around a region of interest, and voxel analysis in the bounding box region. Certain examples facilitate a cloud-shaped stochastic feature-set of a fully-connected network (FCN) in conjunction with multi-layer input features of a CNN using innovative network architectures with gradient boosting machine (GBM) stacking over the FCN and CNN with associated feature sets to segment an image and identify organ(s) in the image.

Deep Learning and Other Machine Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

II. DESCRIPTION OF EXAMPLES

Example Image and Metadata Processing Systems

Figure 2:
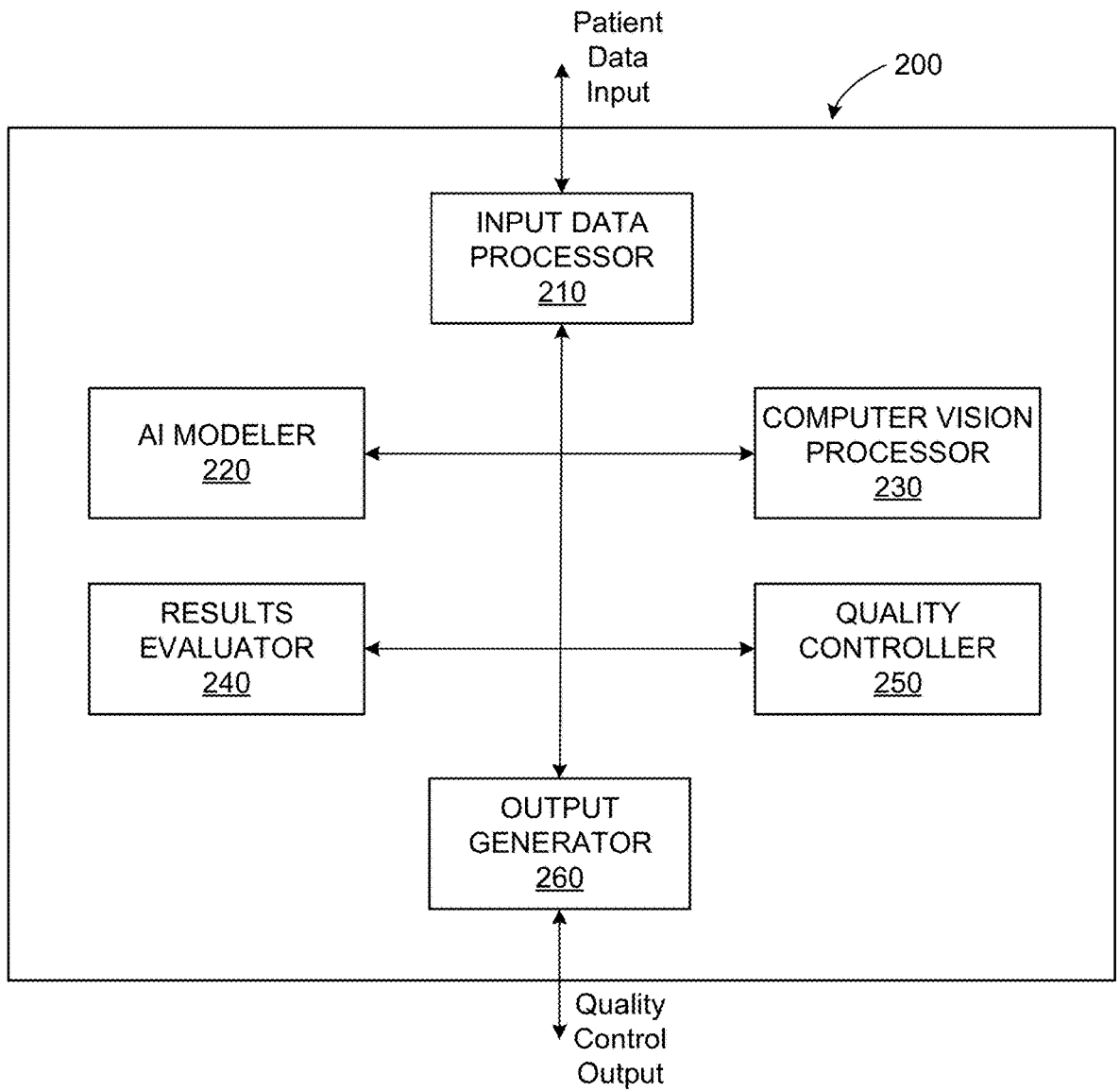
FIG. 2 illustrates an example image quality analysis and control system.

FIG. 2 illustrates an example image quality analysis and control system 200 including an input processor 210, an artificial intelligence (AI) modeler 220, a computer vision processor 230, a results evaluator 240, a quality controller 250, and an output generator 260. The example system 200 processes patient exam record data (e.g., one or more DICOM image files, etc.) using the input processor 210 to identify image data and metadata and separate the image data and metadata for processing.

The image data can be processed using the computer vision processor 230 to identify object(s), feature(s), etc., in the image. The metadata and/or image data can be processed by the AI modeler 220 to correlate image content and non-image information (e.g., features, etc.), verify patient identity, verify region of interest/anatomy of interest, etc. The AI modeler 220 (e.g., including a deep learning network model, other machine learning construct, etc.) and the computer vision processor 230 can be used to identify and process image data features and metadata content and provide information to the results evaluator 240 to detect duplication, validate meta-information, deidentify data, validate content integrity using a checksum, etc. The AI modeler 220 and the computer vision processor 230 can be used together or separately depending on availability of image data, non-image data, preferences/settings, etc.

The results evaluator 240 processes output of the AI modeler 220 and/or the computer vision processor 230 to compare features identified by the computer vision processor 230 and/or the AI modeler 220, evaluate output of the modeler 220 and/or processor 230 to one or more criterion/threshold, identify disparity in an output of the modeler 220 and the processor 230, determine a patient characteristic based on image and non-image data produced by the modeler 220 and the processor 230, etc.

Based on an output of the results evaluator 240, the quality controller 250 determines whether the data is of sufficient quality to be used for diagnosis, treatment, clinical trial, etc. The quality controller 250 can form an overall quality assessment and compare the assessment to one or more pre-defined criterion to verify completeness and quality of image and/or non-image data. The quality controller 250 can determine a quality result based on the automated analysis of the incoming patient data by the AI modeler 220, computer vision processor 230, and results evaluator 240. The output generator 260 can generate a report, route data/results to another system for further processing, store patient data determined to be of sufficient quality in an EMR, PACS, RIS, HIS, etc., display data/results, and/or provide other output based on the processing of the quality controller 250, results evaluator 240, AI modeler, and/or computer vision processor 230.

Example Learning Network Systems

Figure 3:
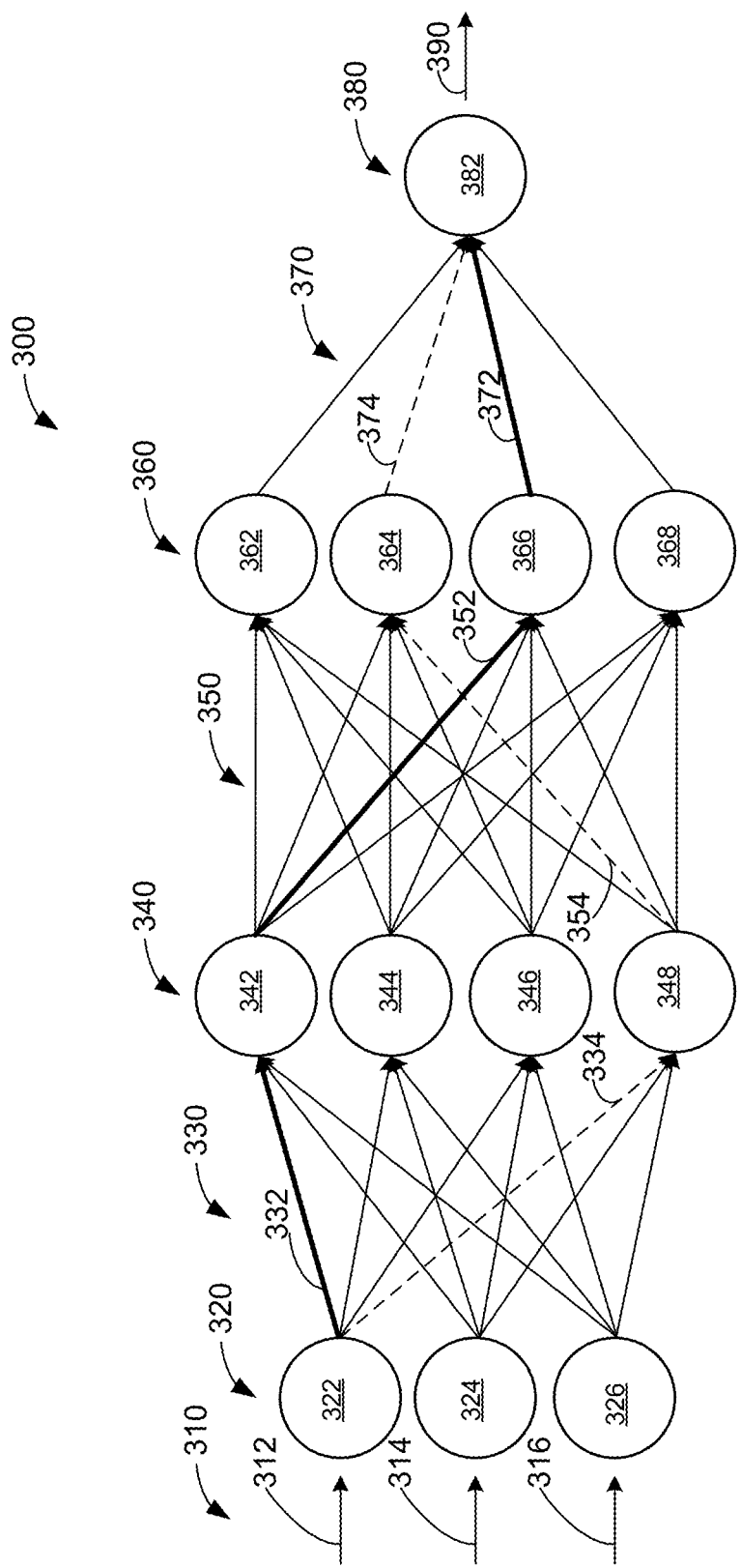
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 and to an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370, certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
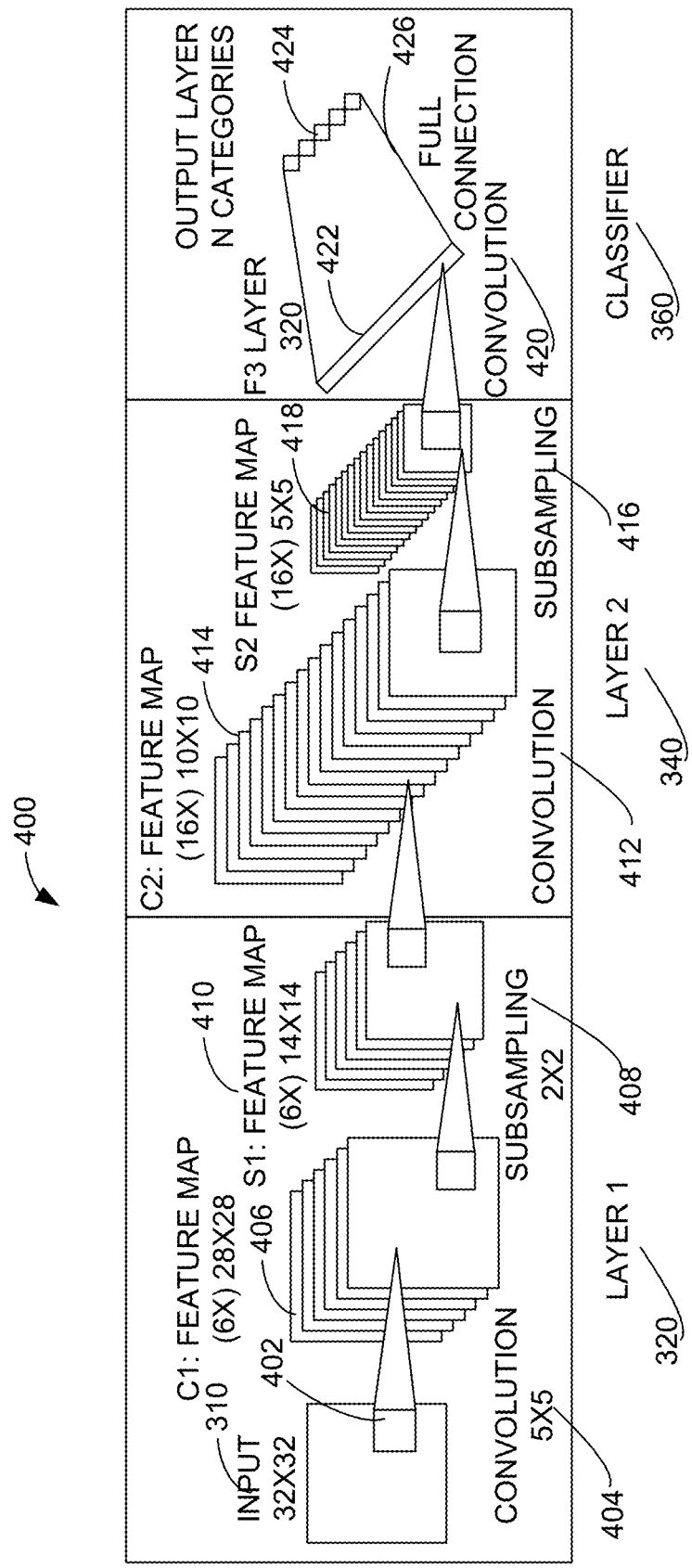
FIG. 4 illustrates a particular implementation of the example neural network as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer e80. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example.

Figure 5:
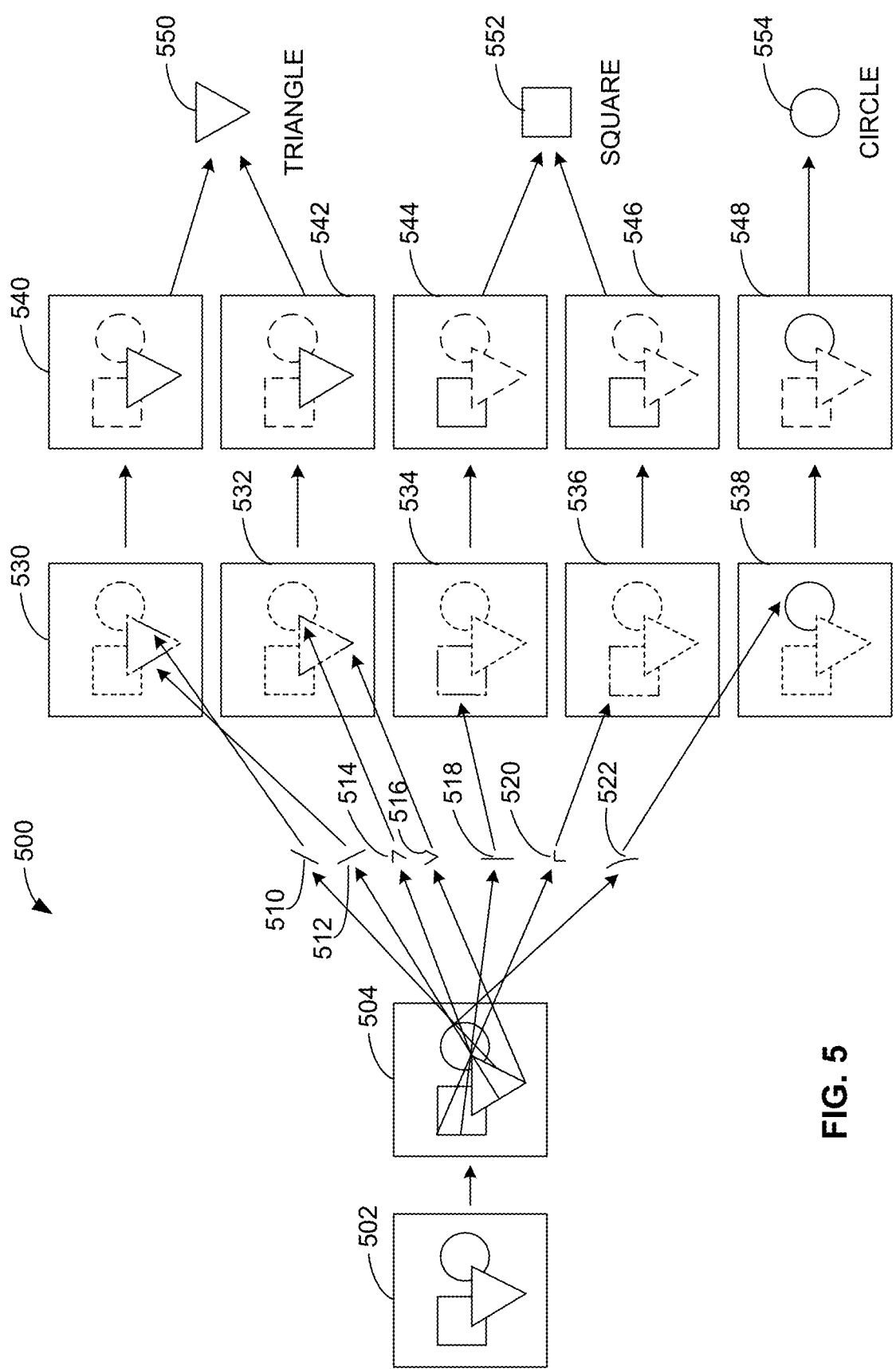
FIG. 5 is a representation of an example implementation of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

Figure 6A:
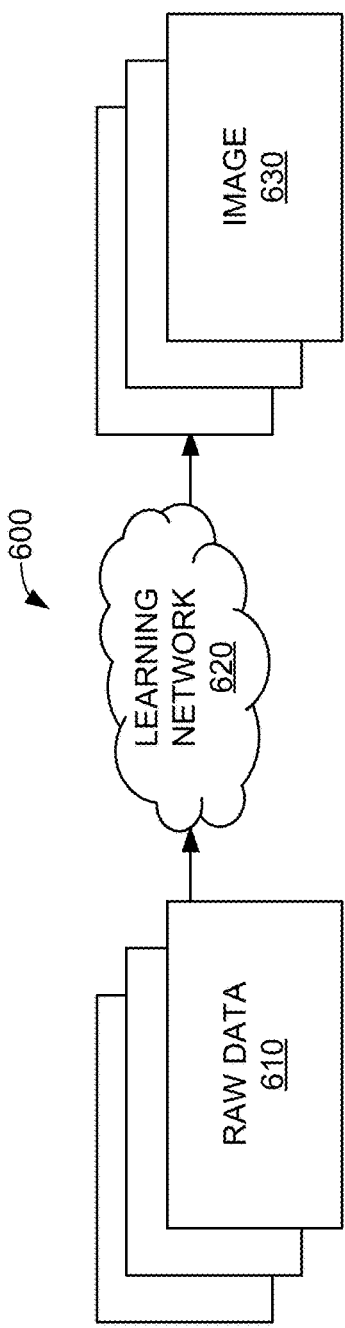
FIG. 6A illustrates an example configuration to apply a learning network to process and/or otherwise evaluate an image.

FIG. 6A illustrates an example configuration 600 to apply a learning (e.g., machine learning, deep learning, etc.) network to process and/or otherwise evaluate an image. Machine learning can be applied to a variety of processes including image acquisition, image reconstruction, image analysis/diagnosis, etc. As shown in the example configuration 600 of FIG. 6A, raw data 610 (e.g., raw data 610 such as sonogram raw data, etc., obtained from an imaging scanner such as an x-ray, computed tomography, ultrasound, magnetic resonance, etc., scanner) is fed into a learning network 620. The learning network 620 processes the data 610 to correlate and/or otherwise combine the raw image data 620 into a resulting image 630 (e.g., a "good quality" image and/or other image providing sufficient quality for diagnosis, etc.). The learning network 620 includes nodes and connections (e.g., pathways) to associate raw data 610 with a finished image 630. The learning network 620 can be a training network that learns the connections and processes feedback to establish connections and identify patterns, for example. The learning network 620 can be a deployed network that is generated from a training network and leverages the connections and patterns established in the training network to take the input raw data 610 and generate the resulting image 630, for example.

Once the learning 620 is trained and produces good images 630 from the raw image data 610, the network 620 can continue the "self-learning" process and refine its performance as it operates. For example, there is "redundancy" in the input data (raw data) 610 and redundancy in the network 620, and the redundancy can be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy can be evaluated to reduce redundancy in the inputs (raw data) 610. Reducing input 610 redundancy can result in savings in scanner hardware, reduced demands on components, and also reduced exposure dose to the patient, for example.

In deployment, the configuration 600 forms a package 600 including an input definition 610, a trained network 620, and an output definition 630. The package 600 can be deployed and installed with respect to another system, such as an imaging system, analysis engine, etc.

Figure 6B:
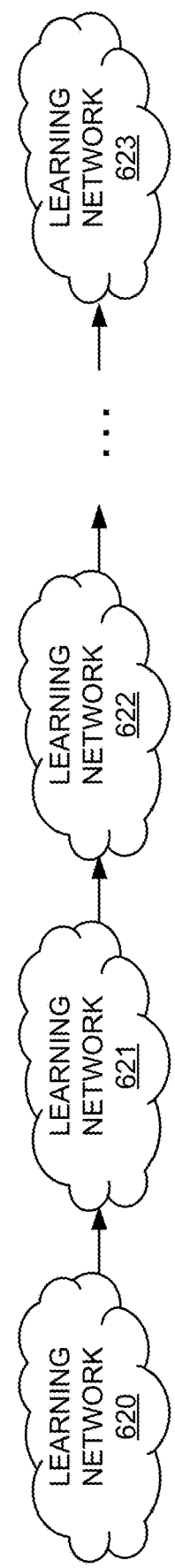
FIG. 6B illustrates a combination of a plurality of learning networks.

As shown in the example of FIG. 6B, the learning network 620 can be chained and/or otherwise combined with a plurality of learning networks 621-623 to form a larger learning network. The combination of networks 620-623 can be used to further refine responses to inputs and/or allocate networks 620-623 to various aspects of a system, for example.

In some examples, in operation, "weak" connections and nodes can initially be set to zero. The learning network 620 then processes its nodes in a retaining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes DLN 621. The learning network 621 is also examined to identify weak connections and nodes and set them to zero. This further retrained network is learning network 622. The example learning network 622 includes the "zeros" in learning network 621 and the new set of nodes and connections. The learning network 622 continues to repeat the processing until a good image quality is reached at a learning network 623, which is referred to as a "minimum viable net (MVN)". The learning network 623 is a MVN because if additional connections or nodes are attempted to be set to zero in learning network 623, image quality can suffer.

Once the MVN has been obtained with the learning network 623, "zero" regions (e.g., dark irregular regions in a graph) are mapped to the input 610. Each dark zone is likely to map to one or a set of parameters in the input space. For example, one of the zero regions may be linked to the number of views and number of channels in the raw data. Since redundancy in the network 623 corresponding to these parameters can be reduced, there is a highly likelihood that the input data can be reduced and generate equally good output. To reduce input data, new sets of raw data that correspond to the reduced parameters are obtained and run through the learning network 621. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI can result in reduced complexity in data acquisition, less demand on system components, reduced stress on patients (e.g., less breath-hold or contrast), and/or reduced dose to patients, for example.

By forcing some of the connections and nodes in the learning networks 620-623 to zero, the network 620-623 to build "collaterals" to compensate. In the process, insight into the topology of the learning network 620-623 is obtained. Note that network 621 and network 622, for example, have different topology since some nodes and/or connections have been forced to zero. This process of effectively removing connections and nodes from the network extends beyond "deep learning" and can be referred to as "deep-deep learning", for example.

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 7:
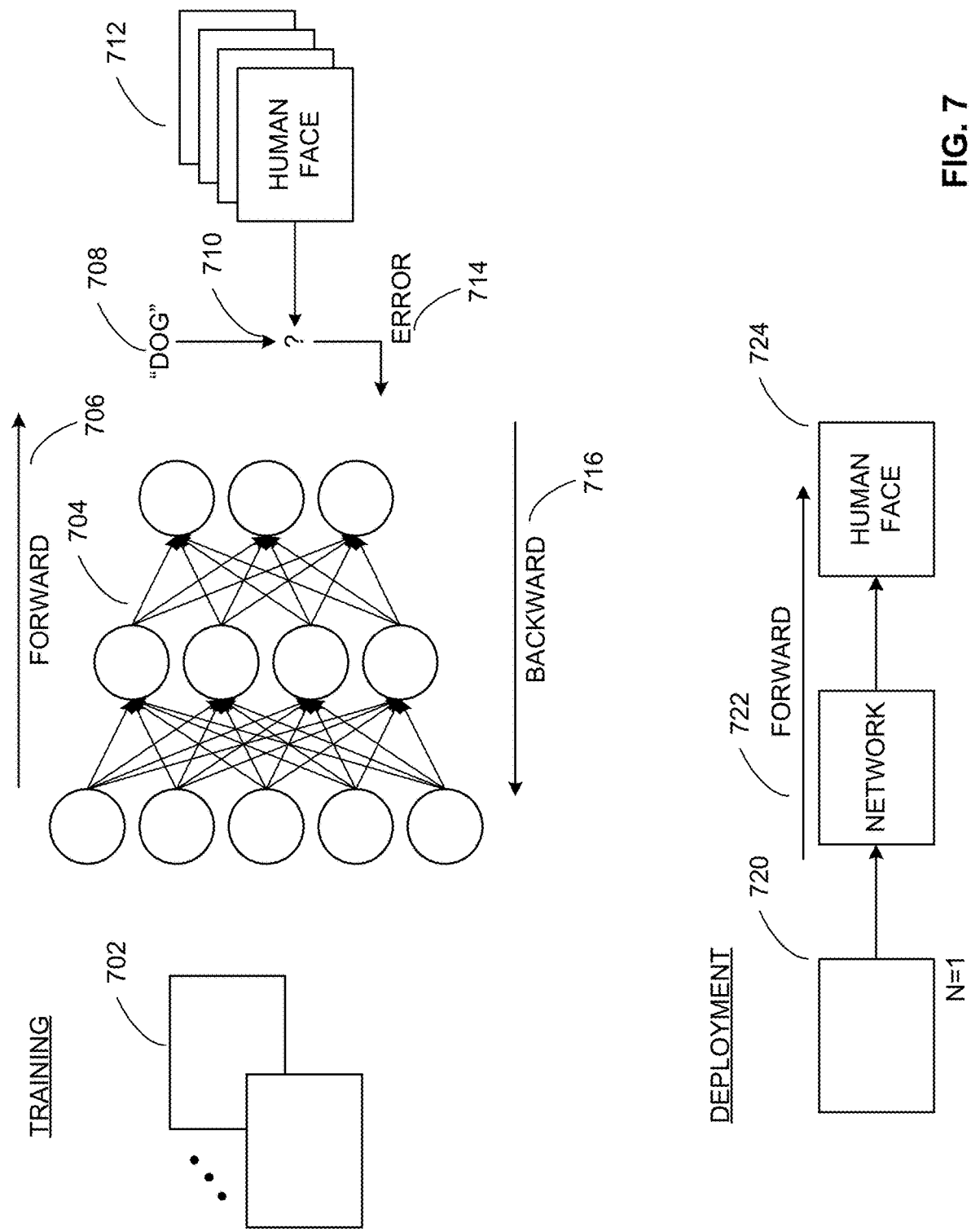
FIG. 7 illustrates example training and deployment phases of a learning network.

FIG. 7 illustrates example training and deployment phases of a learning network, such as a deep learning or other machine learning network. As shown in the example of FIG. 7, in the training phase, a set of inputs 702 is provided to a network 704 for processing. In this example, the set of inputs 702 can include facial features of an image to be identified. The network 704 processes the input 702 in a forward direction 706 to associate data elements and identify patterns. The network 704 determines that the input 702 represents a dog 708. In training, the network result 708 is compared 710 to a known outcome 712. In this example, the known outcome 712 is a human face (e.g., the input data set 702 represents a human face, not a dog face). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Once the comparison of network output 708 to known output 712 matches 710 according to a certain criterion or threshold (e.g., matches n times, matches greater than x percent, etc.), the training network 704 can be used to generate a network for deployment with an external system. Once deployed, a single input 720 is provided to a deployed learning network 722 to generate an output 724. In this case, based on the training network 704, the deployed network 722 determines that the input 720 is an image of a human face 724.

Figure 8:
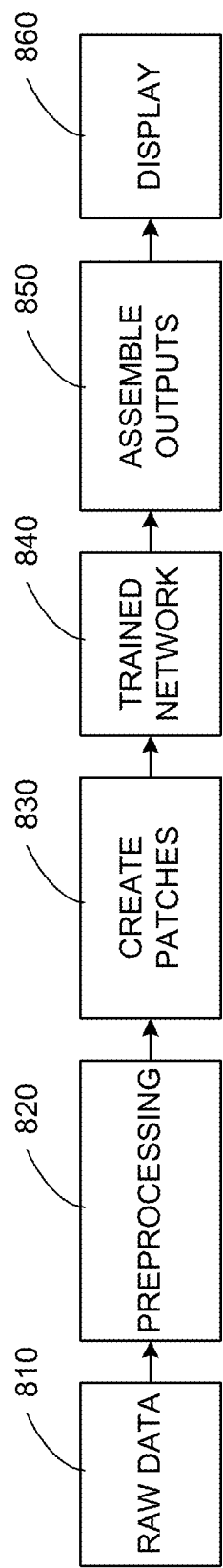
FIG. 8 illustrates an example product leveraging a trained network package to provide a deep learning product offering.

FIG. 8 illustrates an example product leveraging a trained network package to provide a deep and/or other machine learning product offering. As shown in the example of FIG. 8, an input 810 (e.g., raw data) is provided for preprocessing 820. For example, the raw input data 810 is preprocessed 820 to check format, completeness, etc. Once the data 810 has been preprocessed 820, patches are created 830 of the data. For example, patches or portions or "chunks" of data are created 830 with a certain size and format for processing. The patches are then fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device, etc.), etc.).

Figure 9A:
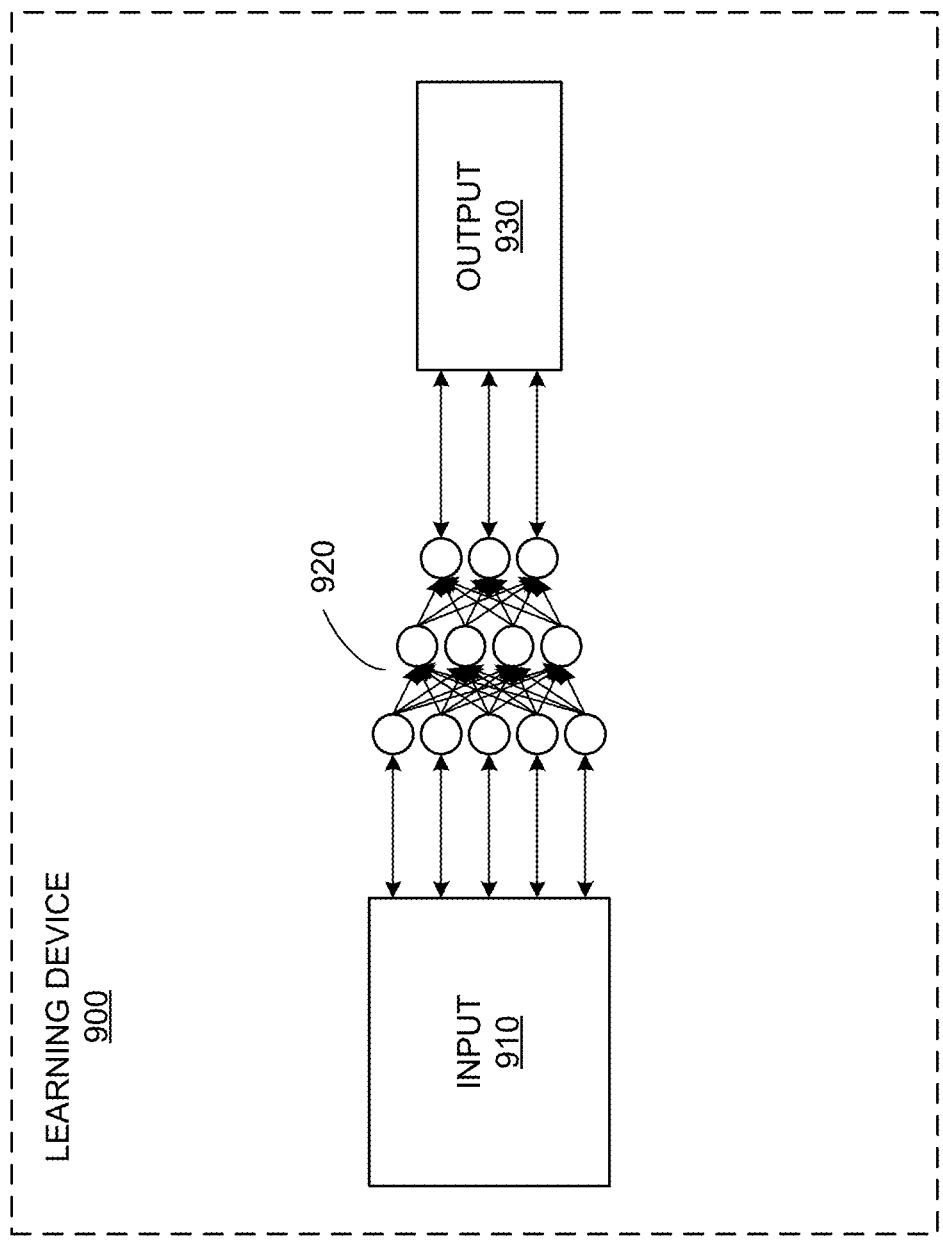
FIGS. 9A-9C illustrate various deep learning device configurations.
Figure 9B:
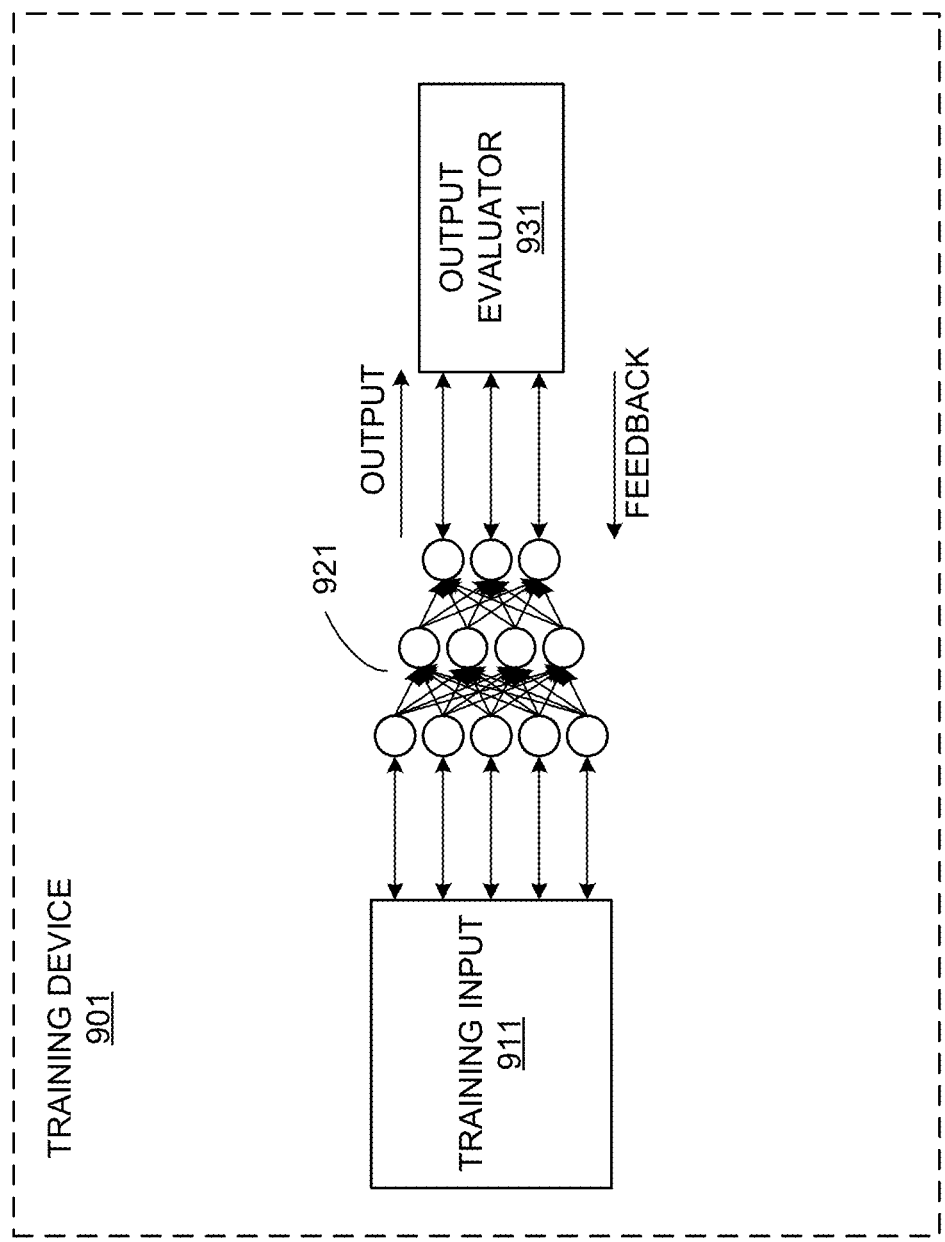
Figure 9C:
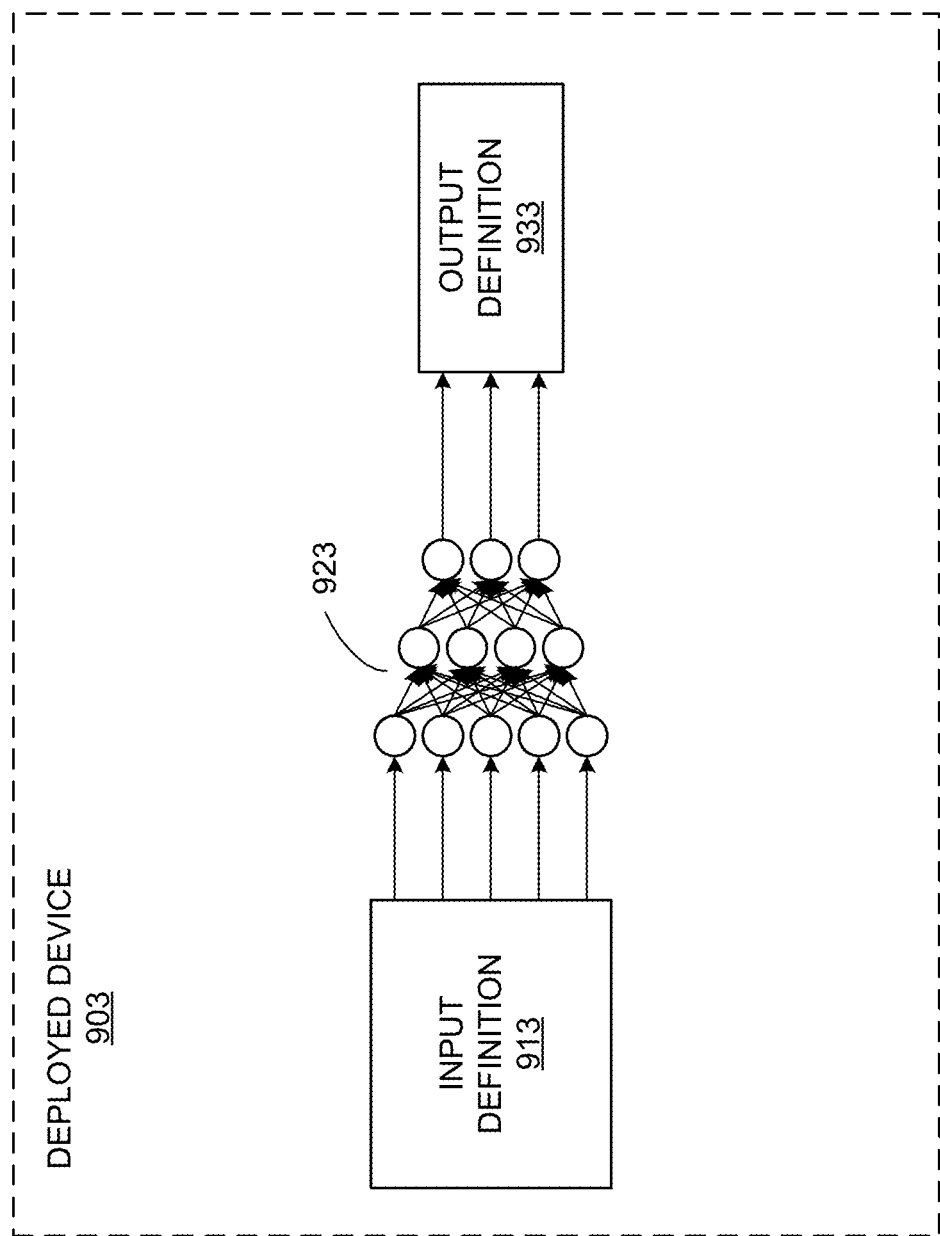

As discussed above, learning networks can be packaged as devices for training, deployment, and application to a variety of systems. FIGS. 9A-9C illustrate various learning device configurations. For example, FIG. 9A shows a general learning device 900. The example device 900 includes an input definition 910, a learning network model 920, and an output definitions 930. The input definition 910 can include one or more inputs translating into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 can be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 can be deployed for use. While the training device 901 processes multiple inputs to learn, the deployed device 903 processes a single input to determine an output, for example. As shown in the example of FIG. 9C, the deployed device 903 includes an input definition 913, a trained network 923, and an output definition 933. The trained network 923 can be generated from the network 921 once the network 921 has been sufficiently trained, for example. The deployed device 903 receives a system input 913 and processes the input 913 via the network 923 to generate an output 933, which can then be used by a system with which the deployed device 903 has been associated, for example.

Example Image and Metadata Processing Systems and Methods

Figure 10:
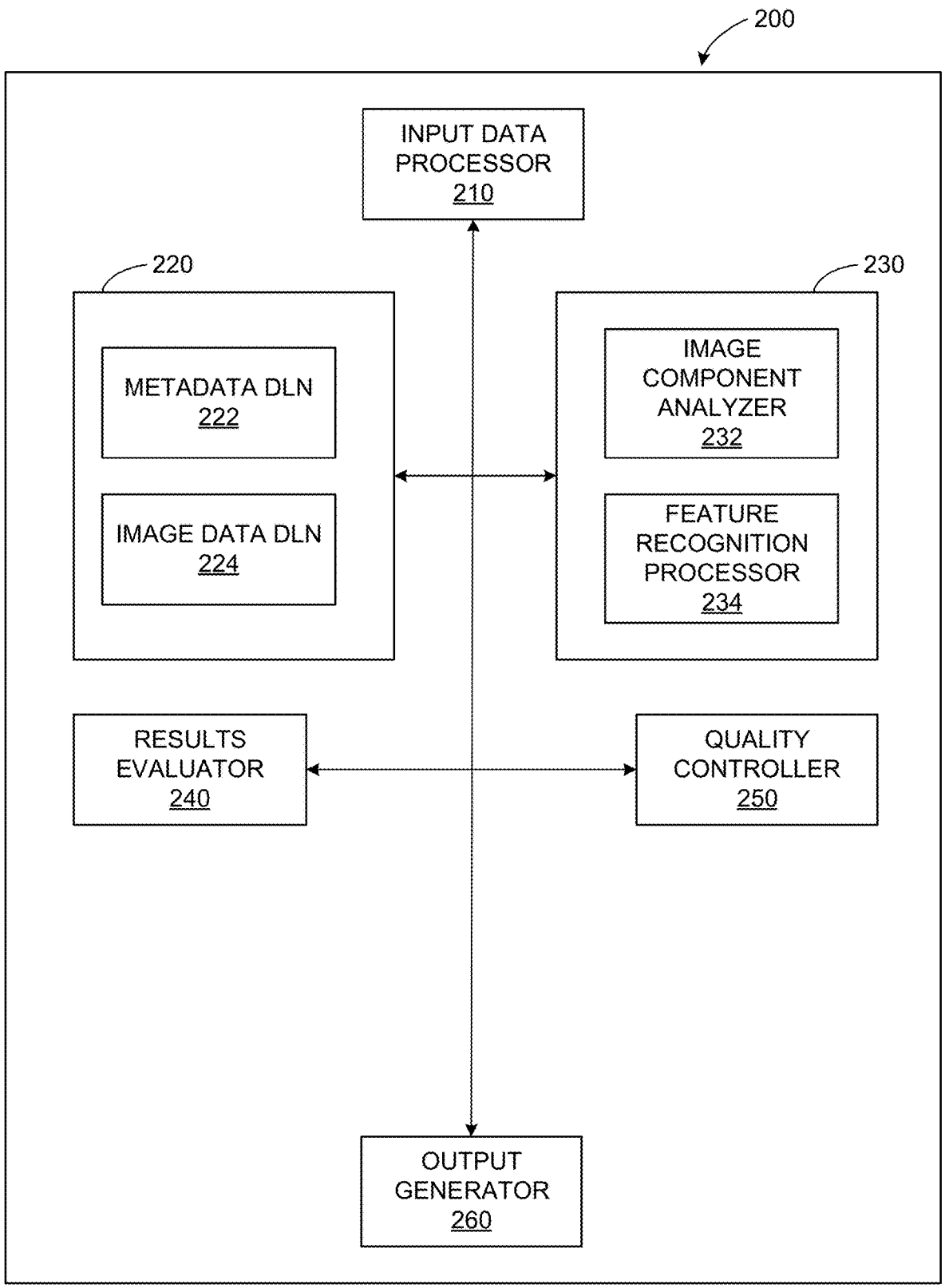
FIG. 10 illustrates an example implementation of the image quality analysis and control system of FIG. 2.

FIG. 10 illustrates an example implementation of the image quality analysis and control system 200. As shown in the example of FIG. 10, the AI modeler 220 can be implemented using a metadata deep learning network (DLN) model 222 and an image data DLN model 224. Thus, health data provided to the AI modeler 220 from the input processor 210, which identified the image data and non-image data (e.g., meta data, other meta information, etc.) can be divided between the two DLN models 222, 224 for processing. In some examples, the two DLN models 222, 224 are implemented together to allow the composite model to evaluate both image and non-image data together as factors in the DLN model to drive an output. In the example of FIG. 10, separate DLN models 222, 224 allow conclusions/evaluations to be drawn regarding the image data and the non-image metadata, which are provided to the results evaluator 240 to determine whether the image data corresponds to the non-image data and/or otherwise satisfies one or more criteria/thresholds defined for the data and a target environment/application (e.g., patient diagnosis, treatment, clinical trial participation, etc.).

In the example of FIG. 10, the computer vision processor 230 includes an image component analyzer 232 and a feature recognition processor 234. The computer vision processor 230 receives image data from the input processor 210, and the image component analyzer 232 analyzes the image data to segment and/or otherwise identify features in the image data. The image component analyzer 232 performs an image component analysis to identify one or more items in the image, such as an anatomy (e.g., kidney, liver, heart, lung, etc.), lesion, other object or area of interest, etc. Components identified in the image by the image component analyzer 232 are provided to the feature recognition processor 234 which processes the identified item(s)/region(s) to identify the content of the item/region (e.g., kidney, liver, heart, lung, chest, head, neck, leg, etc.). The feature recognition processor 234 can provide some analysis of the identified feature as well (e.g., within normal size range, satisfies reference criterion, etc.).

Output feature information from the feature recognition processor 234 to the results evaluator 240 is used by the evaluator 240 in conjunction with image and/or non-image modeler 220 output to correlate and evaluate the health data (e.g., whether a kidney identified in the image by the computer vision processor 230 matches a determination by the AI modeler 220 that the study called for a brain scan, etc.). Outcome(s) from the evaluation/correlation/comparison by the results evaluator 240 are provided to the quality controller 250 to determine whether the outcome(s) indicate that the data is of sufficient quality to be provided for diagnosis, treatment, clinical trial, etc.

While example implementations are illustrated in conjunction with FIGS. 1-10, elements, processes and/or devices illustrated in conjunction with FIGS. 1-10 may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Figure 11:
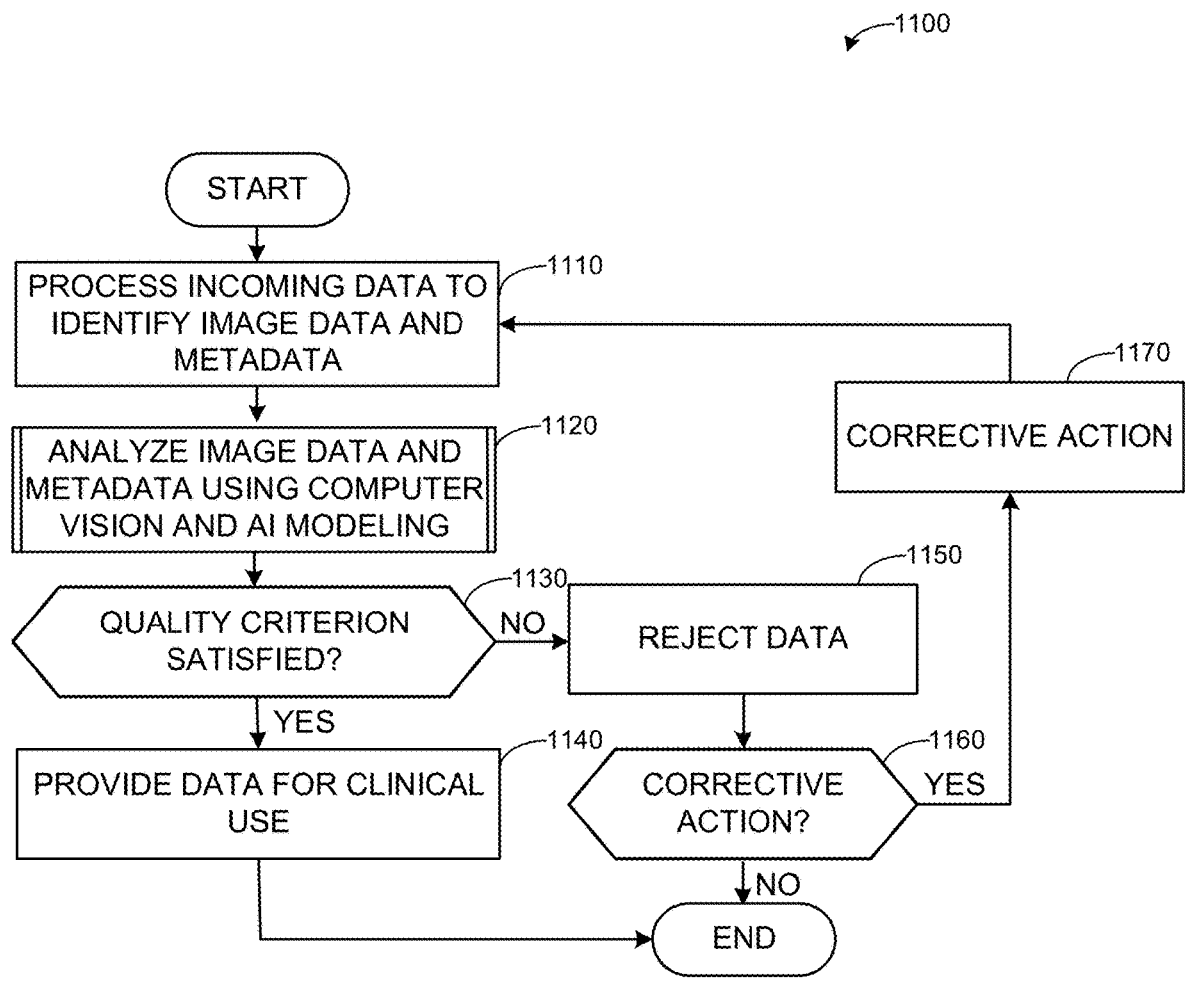
FIGS. 11-12 illustrate flow diagrams of example image quality control processes.
Figure 12:
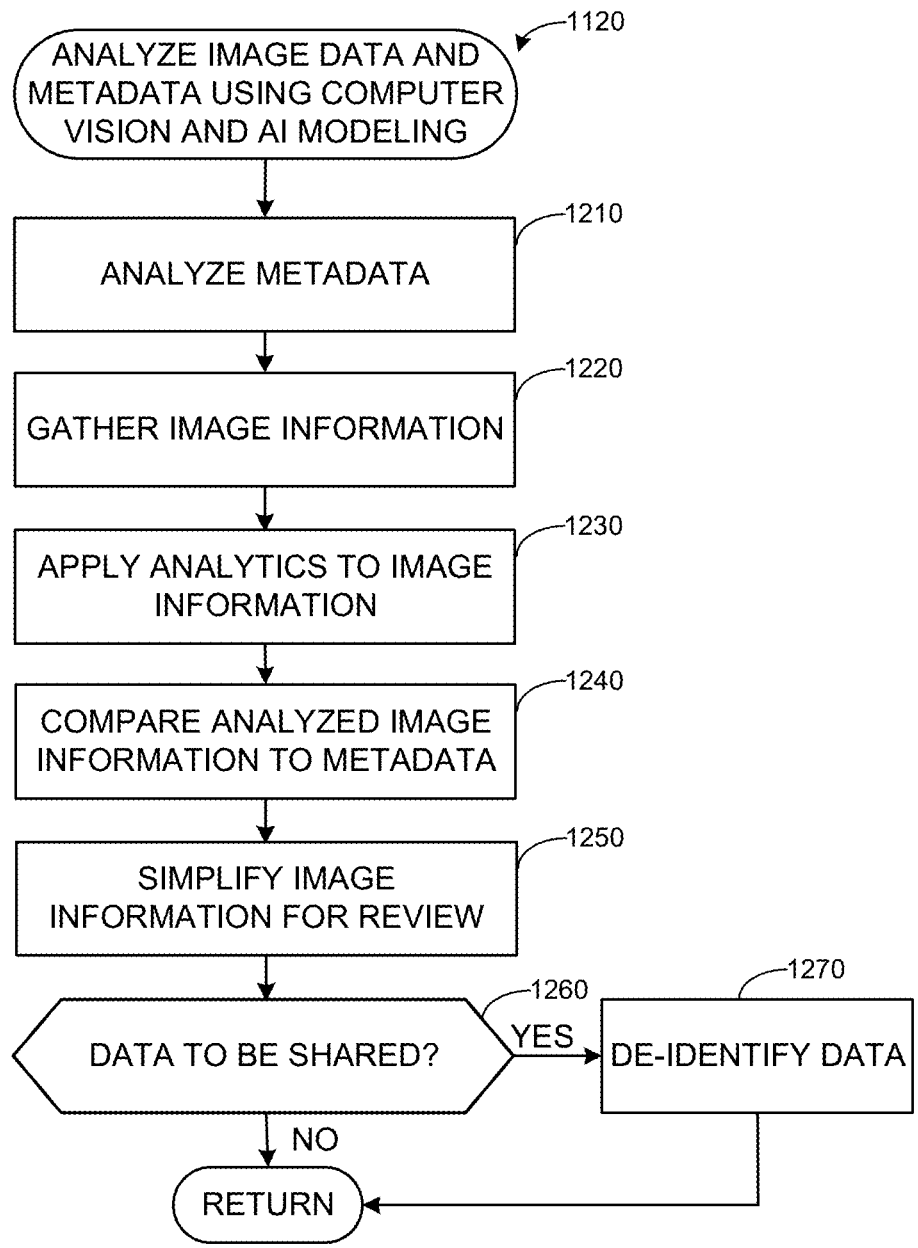

Flowcharts representative of example machine readable instructions for implementing components disclosed and described herein are shown in conjunction with at least FIGS. 11-12. In the examples, the machine readable instructions include a program for execution by a processor such as the processor 1312 shown in the example processor platform 1300 discussed below in connection with FIG. 13. The program may be embodied in machine readable instructions stored on a tangible computer readable storage medium such as a CD-ROM, a floppy disk, a hard drive, a digital versatile disk (DVD), a Blu-ray disk, or a memory associated with the processor 1312, but the entire program and/or parts thereof could alternatively be executed by a device other than the processor 1312 and/or embodied in firmware or dedicated hardware. Further, although the example program is described with reference to the flowcharts illustrated in conjunction with at least FIGS. 11-12, many other methods of implementing the components disclosed and described herein may alternatively be used. For example, the order of execution of the blocks may be changed, and/or some of the blocks described may be changed, eliminated, or combined. Although the flowcharts of at least FIGS. 11-12 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIGS. 11-12 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIGS. 11-12 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

As shown in the example method 1100 depicted in FIG. 11, patient data is processed to determine whether or not the data satisfies one or more quality criterion to use the patient data for a clinical purpose such as patient diagnosis, patient treatment, clinical trial, etc. At block 1110, incoming patient data is processed to identify image data and metadata in the patient data. At block 1120, the image data and metadata are analyzed using computer vision and AI modeling to evaluate the image data and metadata and correlate the image data evaluation results with the metadata evaluation results. At block 1130, results of the computer vision and AI modeling analysis are compared to one or more clinical quality criterion to determine whether the patient data satisfies the quality criterion(-ia). At block 1140, when the patient data satisfies the quality criterion(-ia), the patient data is provided for clinical use (e.g., to a RIS/PACS/EMR/imaging workstation/etc. for patient diagnosis and/or treatment, to a health information system for clinical trial, etc.). At block 1150, when the patient data does not satisfy the quality criterion (-ia), the patient data is rejected. In certain examples, at block 1160, corrective action may be applied. When corrective action is to be applied, at block 1170, corrective action can be taken to adjust the image data and/or metadata, and the patient data can be re-evaluated to determine compliance. For example, metadata can be adjusted to correctly identify image content, metadata can be deidentified, new image data can be acquired and associated with the metadata, etc.

Thus, certain examples facilitate evaluation of data collected from one or more locations (e.g., hospitals, clinics, etc.) with respect to one or more patients. The data includes image data and non-image data (e.g., metadata in a DICOM file header, etc.), and the image content and meta information can be analyzed to help ensure a correlation between the image content and its metadata (e.g., the image content is of the organ/region specified in the metadata, the image slice is of the thickness specified in the metadata, etc.). A deep learning network model can be trained and customized to look for a particular anatomy (e.g., head, chest, abdomen, etc.) in a particular set of image data, for example. Computer vision can also identify the anatomy in the image data. The two techniques can be combined and compared, the anatomy identified by computer vision can be analyzed via a neural network to determine its content, etc. Incorrect and/or uncorrelated content can be flagged for user review and/or triggered for adjustment/corrective action (e.g., metadata can be adjusted to correctly identify image content, metadata can be deidentified, new image data can be acquired and associated with the metadata, etc.).

Certain examples perform motion analysis of the image data and/or apply one or more factors to image and non-image data analysis. Certain examples process electrocardiogram data in conjunction with cardiac images to evaluate uptake and/or trigger timing (e.g., a user pressed the trigger too soon in a heart scan, etc.), etc.

In certain examples, machine learning via the AI modeler 220 includes a supervised learning classifier to classify images into good or bad quality. Such classification can be trained using data collection with annotations, for example. Certain examples provide auto-encoder machine learning models which operate unsupervised with respect to a set of normal images. The model learns what is "normal" or expected, and, when a new image comes in and diverges from the "normal" in pathology, artifact, etc., then the system can adapt the machine learning model to alert that this is an abnormal image, for example.

Certain examples can drive modality behavior with respect to image data acquisition. For example, MRI acquisition parameters can be set automatically by a console machine. Image acquisition can be optimized with respect to certain planes fit to certain anatomy structures inside the planes. The system 200 can process the image data to segment the image based on included structures and set imaging parameters based on the identified structures. A quality check can be built in such that when an acquired magnetic resonance image is processed, deep learning and/or other artificial intelligence is used to determine whether the requested anatomy (e.g., head, liver, knee, etc.) is present in the actual image data, for example. Quality control can be performed on a low resolution image to determine whether or not the image includes the entire anatomy specified (at sufficient processing/diagnostic quality) or is just a partial scan (and/or at insufficient image quality), for example.

Output such as the summary report 100 can be produced showing details regarding the patient data, a simple visual indicator of pass/fail, etc. Output can provide an audit trail to be validated for a clinical trial, patient diagnosis/treatment, etc.

While some examples have been shown and described with respect to CT images, the same systems and methods can be applied to MR, x-ray, MICT, ultrasound, etc. In some examples, modalities can be combined such as applying a CT model to MR images, etc. Quality checks can include an evaluation of resulting image content and related metadata and can be implemented in a separate system, incorporated in an imaging device (e.g., pneumothorax detection for an x-ray device, etc.), integrated into a PACS, RIS, etc.

FIG. 12 illustrates a flow diagram providing further detail regarding an example implementation of analyzing image data and metadata using computer vision and AI modeling to evaluate the image data and metadata and correlate the image data evaluation results with the metadata evaluation results (block 1120) for a DICOM file including image data and metadata. At block 1210, metadata is analyzed from the DICOM file to check for data about the patient, the image, and how the image was acquired, etc. For example, the metadata (e.g., stored in a DICOM header of an image file, embedded with the image data in the file, etc.) can include information that can be configured according to one more settings/criteria, such as patient details, scanner details, scanning parameters, and contextual/clinical information (e.g., contrast, anatomy scanned, etc.), etc. For example, the automated QC process can rely on image metadata generated by the imaging device (e.g., image properties, acquisition parameters, etc.) and validated patient-metadata imported from RIS/HIS, etc.

At block 1220, image information is extracted from the DICOM file. For example, deep learning model(s) can be used to instantiate algorithms to check for features including image quality (low level checks), patient anatomy (medium level checks), and checks about the patient such as obesity (high level checks). For example, image information can include low-level features such as presence of noise, contrast enhancement, artifact, etc., medium-level features such as presence of anatomy region, organ, landmark, etc., high-level features such as presence of obesity, extreme pathology, and implant detection, etc.

At block 1230, analytics are applied to the extracted image information according to one or more criterion. For example, quantitative analytics can be customized to an anatomical structure of interest. Analytics can include detecting/segmenting the structure of interest, extracting feature(s) from the structure such as density, contrast, noise, texture, histogram, etc., and classifying the structure based on the features.

At block 1240, the analyzed image information is compared with the metadata to preserve the integrity of a large dataset. For example, duplication among data files can be detected (e.g., different identifier but same image and/or patient, etc.), meta information can be validated (e.g., a contrast-agent is indicated by the metadata but no contrast is found in the obtained image, etc.), etc.

At block 1250, image information is simplified to facilitate expedited human readability of a large number of images (e.g., visual assessment, search, etc.). For example, standard 2D views can be generated from 3D images (e.g., slice, ray-sum, etc.). A checksum can be generated to provide an indication of the integrity of one or more images and/or can be used to compare two similar images (e.g., do they have a matching checksum?), etc. Thus, image data can be transformed into images with heightened readability for human and/or machine review. In certain examples, the image data is processed differently for human review versus automated machine processing of the image data.

At block 1260, the DICOM file is analyzed to determine whether the data is to be shared (e.g., via clinical trial and/or other sharing of data). If the data is to be shared, then, at block 1270, the data is deidentified. For example, removal of an individual's identification is important in clinical trials, population health data pools, etc. Patient-identifying meta information can be detected and modified (e.g., erase from the DICOM header, replaced with dummy information such as 0000 or xxxx, etc.), for example. Patient-identifying image information can also be identified and modified (e.g., localize and erase a face from an image, remove embedded patient identifier in the image, etc.).

Figure 13:
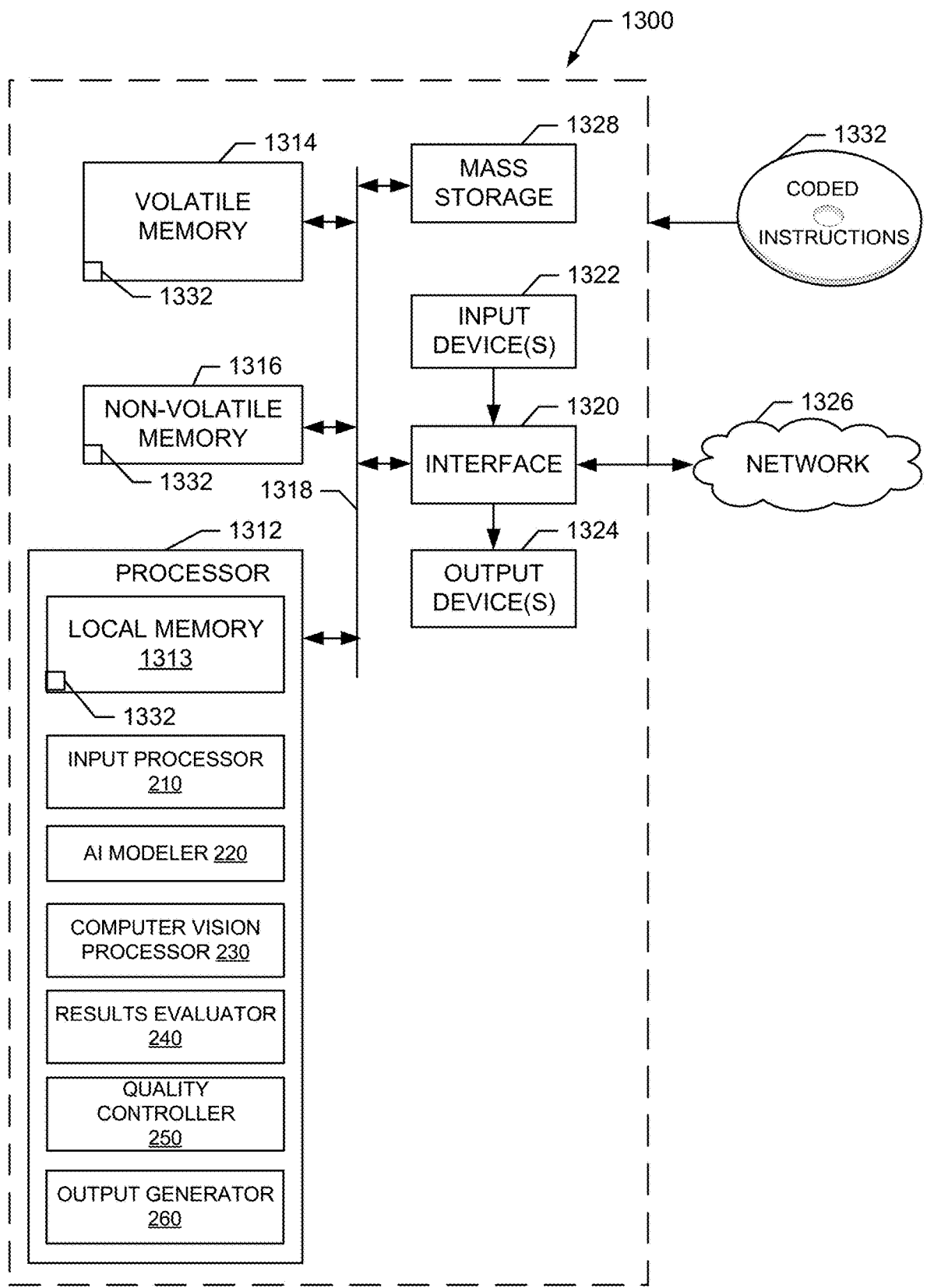
FIG. 13 is a block diagram of a processor platform structured to execute the example machine readable instructions to implement components disclosed and described herein.

FIG. 13 is a block diagram of an example processor platform 1300 structured to executing the instructions of at least FIGS. 11-12 to implement the example components disclosed and described herein. The processor platform 1300 can be, for example, a server, a personal computer, a mobile device (e.g., a cell phone, a smart phone, a tablet such as an iPad™), a personal digital assistant (PDA), an Internet appliance, or any other type of computing device.

The processor platform 1300 of the illustrated example includes a processor 1312. The processor 1312 of the illustrated example is hardware. For example, the processor 1312 can be implemented by integrated circuits, logic circuits, microprocessors or controllers from any desired family or manufacturer.

The processor 1312 of the illustrated example includes a local memory 1313 (e.g., a cache). The example processor 1312 of FIG. 13 executes the instructions of at least FIGS. 11-12 to implement the systems and infrastructure and associated methods of FIGS. 1-10 such as the example input processor 210, artificial intelligence (AI) modeler 220, computer vision processor 230, results evaluator 240, quality controller 250, output generator 260, or, more generally, the image quality analysis and control system 200, etc. The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a clock controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1312. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIG. 13 may be stored in the mass storage device 1328, in the volatile memory 1314, in the non-volatile memory 1316, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques. Certain examples improve computing technology through the addition of a computer vision processor and one or more AI models to transform image data and metadata into quality indicators for quality control analysis and output.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An automated image quality control system comprising:
   an artificial intelligence modeler to process image data and metadata from patient data to generate one or more first features from the image data and to parse the metadata to identify study information;
   a computer vision processor to identify one or more second features in the image data;
   a results evaluator to compare the one or more first features and the one or more second features to generate a comparison and to evaluate the comparison, the one or more first features, and the one or more second features with respect to the study information to generate an evaluation;
   a quality controller to compare the evaluation to one or more quality criterion to produce an approval or rejection of the patient data; and
   an output generator to output a representation of the approval or the rejection of the patient data, wherein the approval is to trigger release of the patient data and the rejection is to deny release of the patient data.

2. The system of claim 1, wherein the quality controller is to identify one or more inconsistencies between the evaluation and the one or more quality criterion, and wherein the output generator is to output the one or more inconsistencies.

3. The system of claim 2, wherein the output generator is to output the representation and the one or more inconsistencies in a report.

4. The system of claim 1, wherein the results evaluator is to simplify the image to generate a simplified image for review.

5. The system of claim 1, wherein the results evaluator is to deidentify the patient data to remove a patient identifier from the patient data.

6. The system of claim 1, wherein the one or more first features and the one or more second features include one or more low-level features, medium-level features, or high-level features.

7. The system of claim 6, wherein the metadata includes an identification of one or more low-level features, medium-level features, or high-level features.

8. At least one non-transitory computer-readable storage medium including instructions which, when executed, cause at least one processor to at least:
generate, using a first artificial intelligence model, one or more first features from image data included in patient data;
parse, using a second artificial intelligence model, metadata included in the patient data to identify study information;
identify, using computer vision, one or more second features in the image data;
compare the one or more first features and the one or more second features to generate a comparison;
evaluate the comparison, the one or more first features, and the one or more second features with respect to the study information to generate an evaluation;
compare the evaluation to one or more quality criterion to produce an approval or rejection of the patient data; and
output a representation of the approval or the rejection of the patient data, wherein the approval is to trigger release of the patient data and the rejection is to deny release of the patient data.

9. The at least one computer-readable storage medium of claim 8, wherein the instructions, when executed, cause the at least one processor to identify one or more inconsistencies between the evaluation and the one or more quality criterion, and to output the one or more inconsistencies.

10. The at least one computer-readable storage medium of claim 9, wherein the instructions, when executed, cause the at least one processor to output the representation and the one or more inconsistencies in a report.

11. The at least one computer-readable storage medium of claim 8, wherein the instructions, when executed, cause the at least one processor to simplify the image to generate a simplified image for review.

12. The at least one computer-readable storage medium of claim 8, wherein the instructions, when executed, cause the at least one processor to deidentify the patient data to remove a patient identifier from the patient data.

13. The at least one computer-readable storage medium of claim 8, wherein the one or more first features and the one or more second features include one or more low-level features, medium-level features, or high-level features.

14. The at least one computer-readable storage medium of claim 13, wherein the metadata includes an identification of one or more low-level features, medium-level features, or high-level features.

15. A computer-implemented method of image quality control, the method comprising:
generating, using a first artificial intelligence model, one or more first features from image data included in patient data;
parsing, using a second artificial intelligence model, metadata included in the patient data to identify study information;
identifying, using computer vision, one or more second features in the image data;
comparing, using at least one processor, the one or more first features and the one or more second features to generate a comparison;
evaluating, using the at least one processor, the comparison, the one or more first features, and the one or more second features with respect to the study information to generate an evaluation;
comparing, using the at least one processor, the evaluation to one or more quality criterion to produce an approval or rejection of the patient data; and
outputting, using the at least one processor, a representation of the approval or the rejection of the patient data, wherein the approval is to trigger release of the patient data and the rejection is to deny release of the patient data.

16. The method of claim 15, further including identifying one or more inconsistencies between the evaluation and the one or more quality criterion, and outputting the one or more inconsistencies.

17. The method of claim 15, further including simplifying the image to generate a simplified image for review.

18. The method of claim 15, further including deidentifying the patient data to remove a patient identifier from the patient data.

19. The method of claim 15, wherein the one or more first features and the one or more second features include one or more low-level features, medium-level features, or high-level features.

20. The method of claim 19, wherein the metadata includes an identification of one or more low-level features, medium-level features, or high-level features.

* * * * *